(12) United States Patent
Bosselmann et al.

(10) Patent No.: US 7,908,923 B2
(45) Date of Patent: Mar. 22, 2011

(54) METHOD OF NON-DESTRUCTIVELY TESTING A WORK PIECE AND NON-DESTRUCTIVE TESTING ARRANGEMENT

(75) Inventors: Thomas Bosselmann, Marloffstein (DE); Henrik Stiesdal, Odense C (DK)

(73) Assignee: Siemens Aktiengesellschaft, Munich (DE)

( * ) Notice: Subject to any disclaimer, the term of this patent is extended or adjusted under 35 U.S.C. 154(b) by 660 days.

(21) Appl. No.: 11/998,394

(22) Filed: Nov. 29, 2007

(65) Prior Publication Data
US 2008/0141778 A1   Jun. 19, 2008

(30) Foreign Application Priority Data

Dec. 7, 2006  (DE) .......................... 10 2006 057 765
Apr. 4, 2007  (EP) ..................................... 07007087

(51) Int. Cl.
*G01H 1/00* (2006.01)
(52) U.S. Cl. ................. 73/584; 73/633; 702/33
(58) Field of Classification Search ............... 73/601, 73/633, 584, 587, 602, 645, 649
See application file for complete search history.

(56) References Cited

U.S. PATENT DOCUMENTS

| | | | | |
|---|---|---|---|---|
| 2,591,757 A * | 4/1952 | Young | ............................ | 416/95 |
| 4,474,536 A * | 10/1984 | Gougeon et al. | ............. | 416/226 |
| 5,047,990 A * | 9/1991 | Gafos et al. | ......................... | 367/6 |
| 5,095,744 A * | 3/1992 | Macecek et al. | ................ | 73/146 |
| 5,715,167 A * | 2/1998 | Gupta et al. | ................... | 700/186 |
| 6,317,387 B1 * | 11/2001 | D'Amaddio et al. | ......... | 367/129 |
| 6,378,387 B1 * | 4/2002 | Froom | ......................... | 73/865.8 |
| 6,832,513 B2 * | 12/2004 | Weiss | ............................... | 73/146 |
| 7,057,548 B1 * | 6/2006 | Roberts | ........................... | 342/22 |
| 7,608,939 B2 * | 10/2009 | Bagepalli et al. | ............... | 290/55 |
| 7,740,453 B2 * | 6/2010 | Zirin et al. | .................... | 416/226 |
| 2003/0188574 A1 * | 10/2003 | Weiss | ............................... | 73/146 |

(Continued)

FOREIGN PATENT DOCUMENTS

DE     10 2004 061 870 B3     6/2006

(Continued)

OTHER PUBLICATIONS

Translation of DE 10259653 B3.*

(Continued)

*Primary Examiner* — Hezron Williams
*Assistant Examiner* — Samir M Shah

(57) ABSTRACT

A method of non-destructively testing a work piece is disclosed, wherein the work piece is placed within an active field of a positioning system; a frame of reference of the work piece is established based on the geometry of the work piece in the coordinates of the positioning system; the geometry of the work piece is detected by determining the position of specific transponders, which are fixed to the work piece, by the positioning system or the geometry of the work piece is detected by scanning at least parts of the contour of the work piece with a transponder of the positioning system; testing data is acquired for the work piece with a non-destructive testing probe, which comprises a transponder of the positioning system, while the position of the testing probe is recorded by the positioning system; the position of the testing probe is transformed into an intrinsic position defined with respect to the frame of reference of the work piece; and the intrinsic position of the testing probe is assigned to the testing data recorded at the respective position. Moreover, a non-destructive testing arrangement is provided.

9 Claims, 6 Drawing Sheets

U.S. PATENT DOCUMENTS

| | | | |
|---|---|---|---|
| 2004/0145754 A1* | 7/2004 | Dickinson et al. | 356/614 |
| 2005/0111011 A1* | 5/2005 | Dickinson et al. | 356/614 |
| 2006/0162456 A1* | 7/2006 | Kennedy et al. | 73/620 |
| 2006/0188378 A1* | 8/2006 | Bech et al. | 416/227 R |
| 2006/0225278 A1* | 10/2006 | Lin et al. | 29/889.72 |
| 2007/0151375 A1* | 7/2007 | Kennedy et al. | 73/866.5 |
| 2010/0208247 A1* | 8/2010 | Bosselmann et al. | 356/237.1 |

FOREIGN PATENT DOCUMENTS

| | | |
|---|---|---|
| WO | WO 03/069324 A1 | 8/2003 |

OTHER PUBLICATIONS

Translation of DE 10259653 B3, Apr. 29, 2004.*

Pepper+Fuchs GmbH, "VDM35-30-R/20/105/122 Montage—and Bedienungsanleitung", Mar. 24, 2006, Mannheim, Germany, XP002445384, pp. 1-2.

Hui Tong and Seyed A. Zekavat, "Wireless Local Positioning System via DS-CDMA and Beamforming: A Perturbation Analysis", IEEE Communications Society, 2005, XP002445386, pp. 819-823.

* cited by examiner

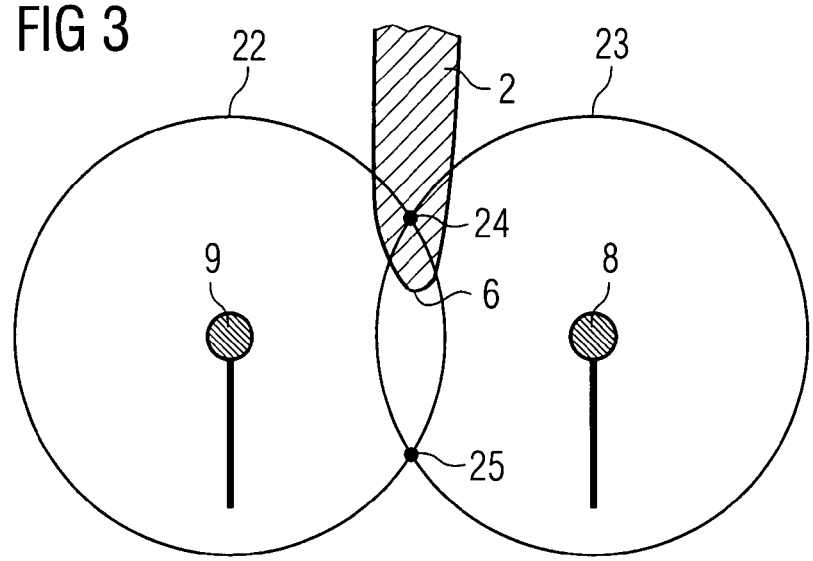
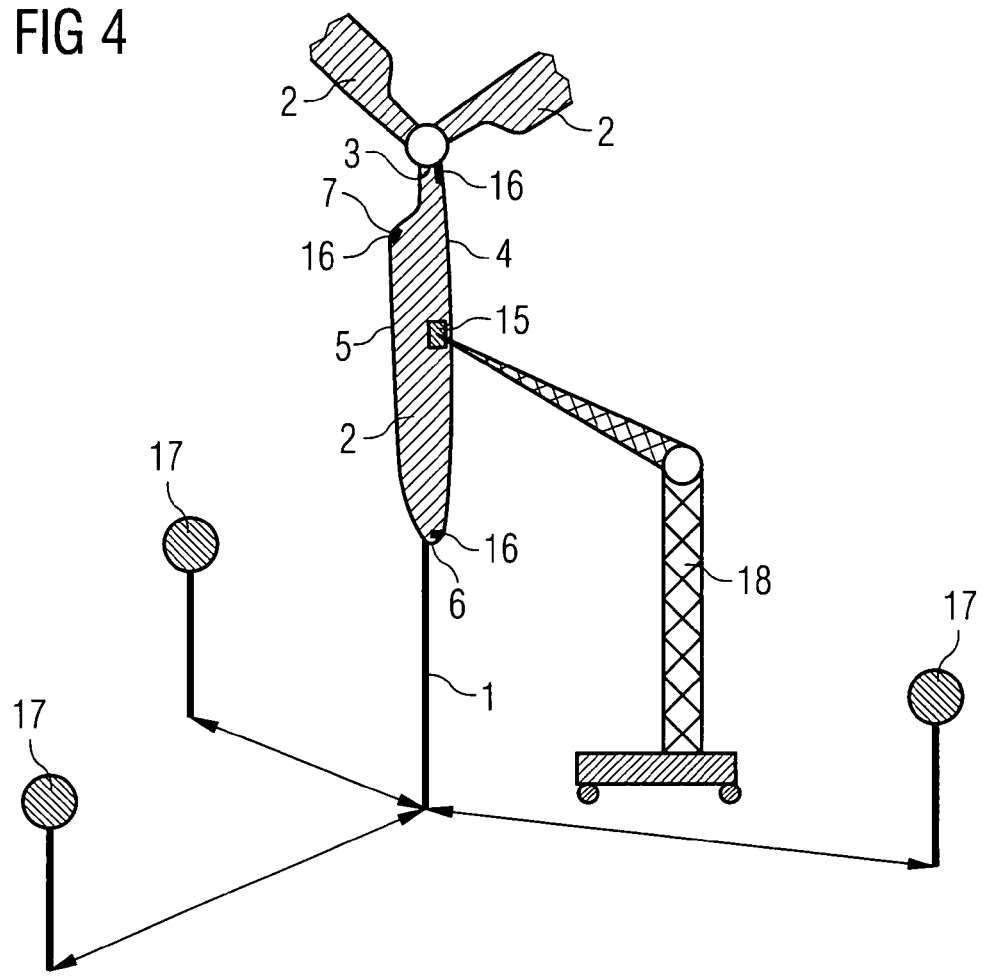

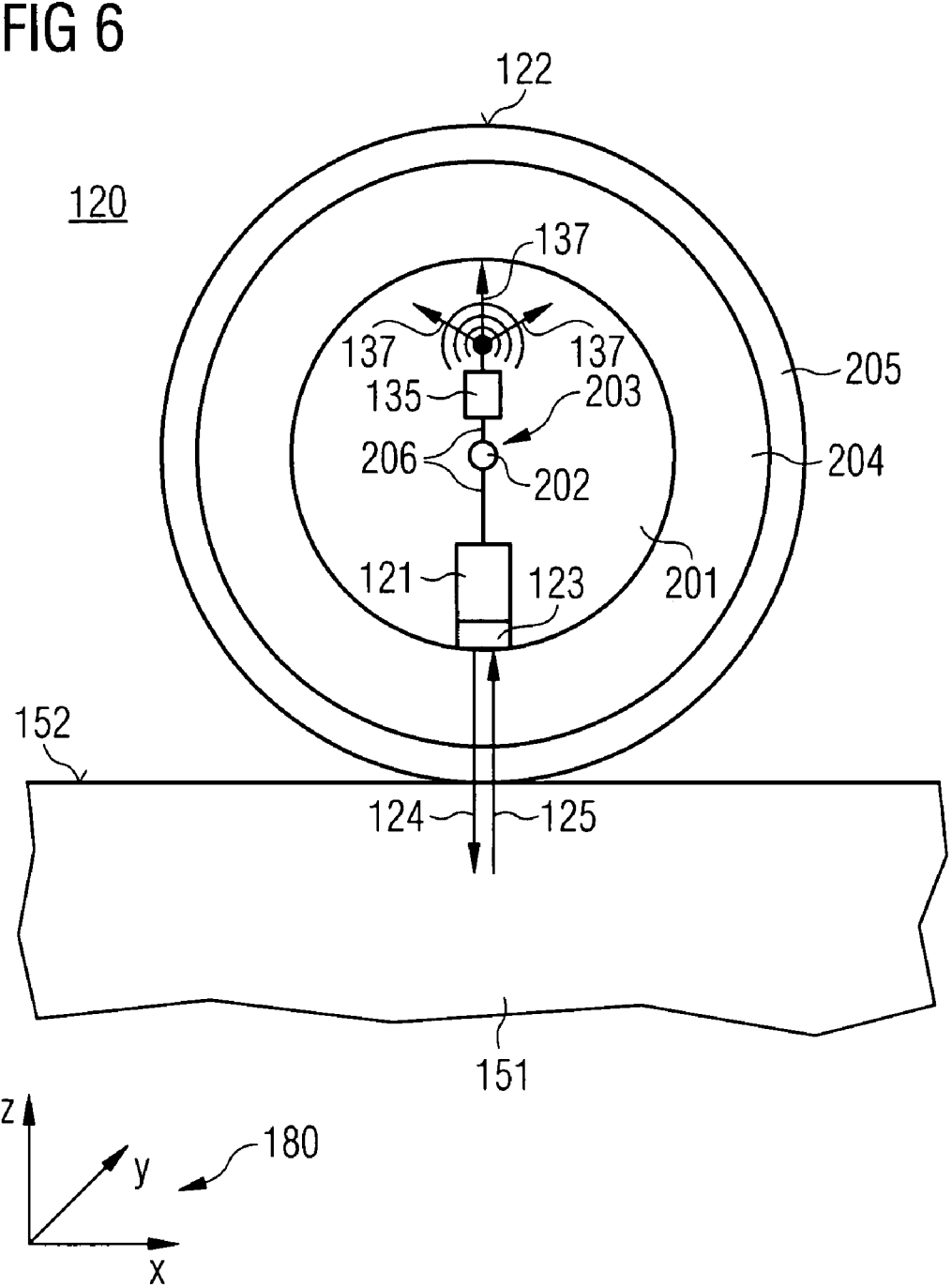

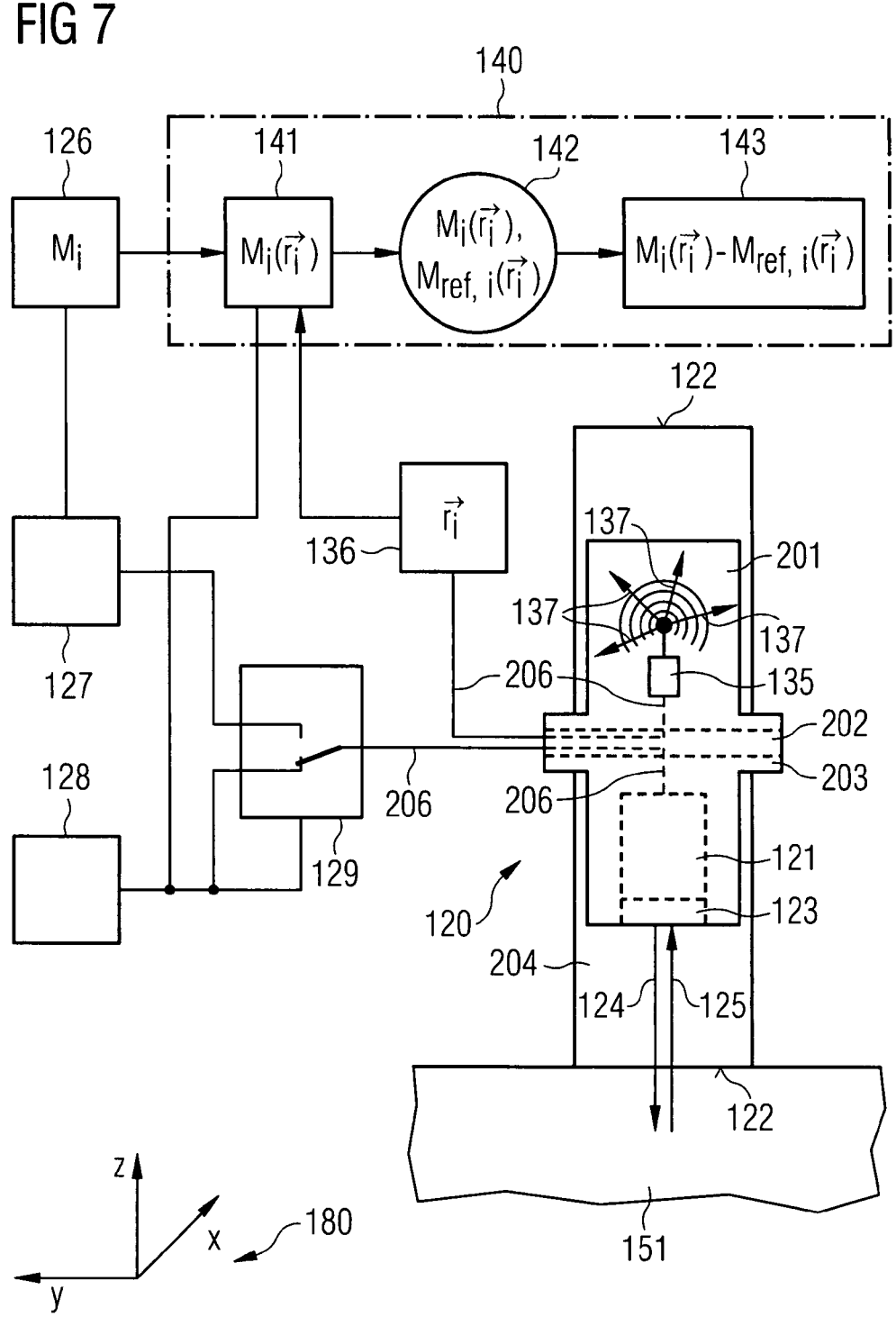

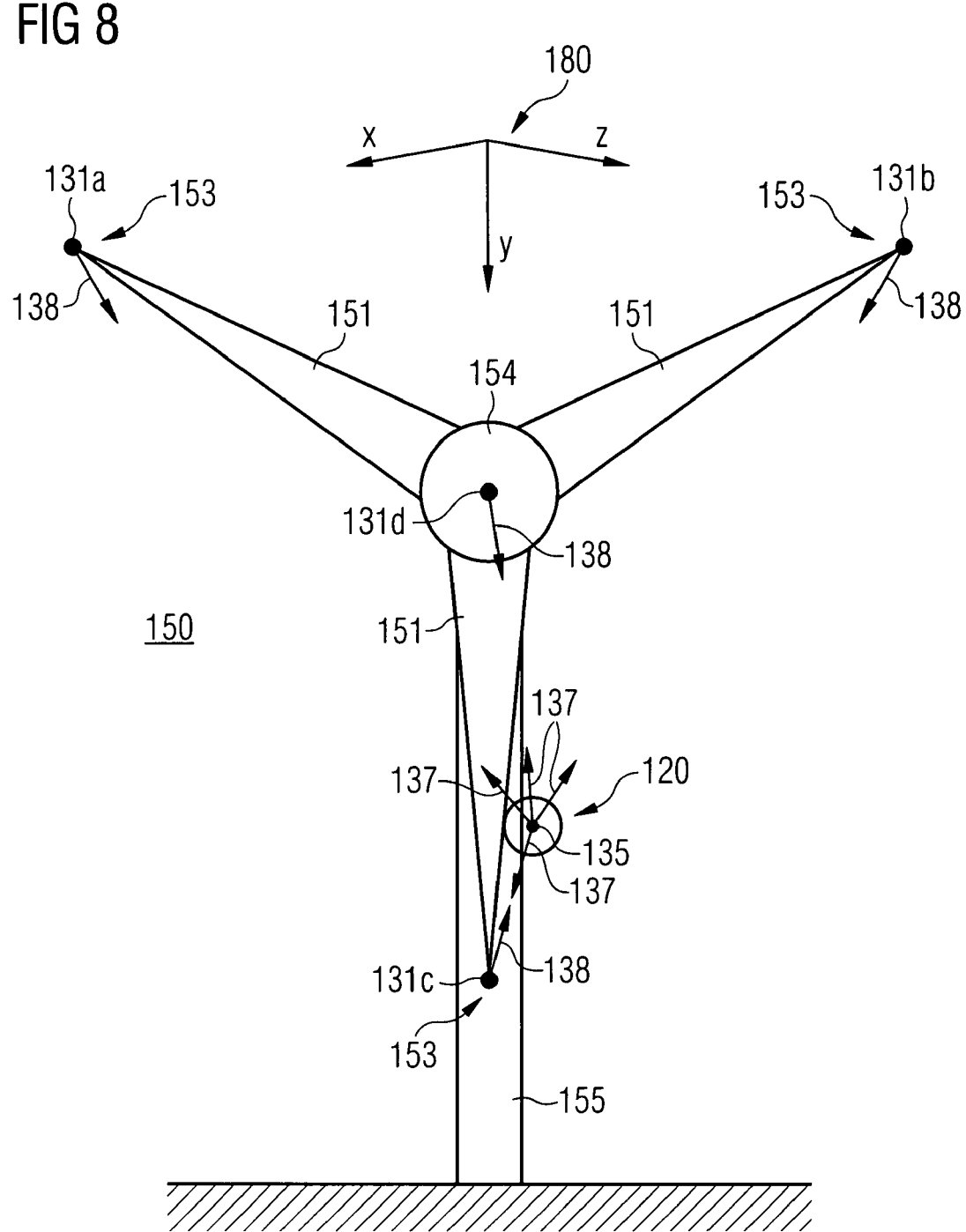

METHOD OF NON-DESTRUCTIVELY TESTING A WORK PIECE AND NON-DESTRUCTIVE TESTING ARRANGEMENT

CROSS REFERENCE TO RELATED APPLICATIONS

This application claims priority of European Patent Office application No. 07007087.5 EP filed Apr. 4, 2007, and claims priority of German application No. 10 2006 057 765.5 EP filed Dec. 7, 2006, both of the applications are incorporated by reference herein in their entirety.

FIELD OF INVENTION

The present invention relates to a method of non-destructively testing a work piece and a non-destructive testing arrangement. The present invention further relates to a method for acoustically testing a work piece and a system for acoustically testing a work piece.

BACKGROUND OF INVENTION

In non-destructive testing (NDT) of large structures, in particular wind turbine blades, a non-destructive testing readout corresponds to a non-destructive testing probe position. Often the exact position is required for further applications, such as repairs or inspections. Possibly such applications are realised at a later date than the non-destructive testing.

Generally the determination of the position of a non-destructive testing probe and the recovery of a particular position can be realised by optical or other marking on the structure where the original testing has been performed. Such marking should unambiguously correlate to a particular non-destructive testing readout and should be recognisable for different persons. Moreover, the marking should be non-destructive, but also resistant against different environmental influences. These requirements are difficult to reach.

Another possibility is the use of large two-dimensional scanners, for instance arrays of non-destructive testing probes that are guided automatically over the surface to be scanned. This arrangement requires the positioning of the structure to be tested in a specific fixture, which reduces flexibility and causes risk of constraints.

A modern wind turbine typically comprises a tower, a nacelle which is rotatably mounted onto the tower, and a rotor which is mounted onto the nacelle. Criteria for concept development and improvement of wind turbines are a high efficiency, minimal acoustic emission, small material usage, and a high lifetime. Large wind turbines are installed off-shore because of the extensive foundation. Such wind turbines typically have a rotor with a diameter up to 130 m. Especially the rotor blades are exposed to enormous load changes. The rotor blades typically have a lifetime between 15 and 20 years. The increasing rotor diameters require improved material properties.

Rotor blades are usually made of composite materials, for instance glass-fibre reinforced plastic (GRP). During the manufacturing process it is difficult to achieve a force-fit connexion between all inner components, for example between the upper and lower housing. It can be necessary that the rotor blade body has to be evacuated and subsequently be immersed in resin. Thereby air inclusions may occur, which may decrease the stability of the rotor blade. In this case delaminations can occur or cracks may be formed, especially at high loads.

The quality of rotor blades is usually controlled after finishing the manufacturing process and after mounting the rotor blades onto the hub of the wind turbine. After mounting the control is performed by optical means, for example by making photos of the observed defects. In this case it is not possible directly to compare the material properties of the rotor blades after manufacturing and after mounting onto the wind turbine.

In DE 102 59 653 B3 a method and a device for non-destructively testing a work piece by means of ultrasound is disclosed, wherein the work piece is scanned by sound using at least two synchronised transponders for ultrasound which are arranged opposite to each other at different sides of the work piece. The transponders for ultrasound and/or the work piece can be moved in relation to each other.

In PEPPERL+FUCHS GmbH "VDM35-30R/20/105/122 Montage-und Bedienungsanleitung" 14 Mar. 2006 (Mar. 14, 2006), PEPPERL+FUCHS GmbH Mannheim, XP002445384, a laser positioning system with a reflector which works in the necessary distance range is disclosed. The laser emits directional radiation, and the direction can be controlled by simply turning the device.

In DE 10 2004 044 342 B4 a method and a device for automatically testing a beam welded connexion between a duct and a stub by means of ultrasound are disclosed. The used ultrasonic testing probe can be moved along the work piece, especially along the weld, according to previously recorded data concerning the geometry of the work piece.

In DE 103 32 457 A1 a method and a device for determining the position of a moving object by measuring the propagation delay of waves are disclosed. The waves are emitted from a transmitter assigned to the moving object. The emitted waves are received by at least two receivers at a known position.

In WO 2005/119054 A1 a method and a device for performing quality control of a rotor blade of an electricity-producing wind power station is disclosed. The device is configured so as to travel along and examine the rotor blade in an automatic or remote-controlled manner.

In DE 10 2004 061 870 B3 a sensor wheel for the acoustic inspection of a measuring object is disclosed. Said sensor wheel comprises an ultrasound-permeable and sufficiently solid hollow roll that is provided with two rim rings and has a bearing surface that can be placed on the measuring object. The sensor wheel is provided with two wheel discs and an axle that has a cylindrical container that is radially flared outward inside the sensor wheel and that has an at least partially ultrasound-permeable surface of the cylinder. The sensor wheel also comprises an ultrasound-permeable liquid coupling agent between the roll and the container, said container having at least one ultrasound-producing sound transducer. The ultrasonic waves can be emitted through the coupling agent, the roll and the bearing surface into the measuring object. The sensor wheel is suitable for use in the inspection of railroad tracks and/or railroad wheels.

SUMMARY OF INVENTION

It is an objective of the present invention to provide a method that allows a determination as well as a recovery of a particular position of a non-destructive testing probe. It is a second objective to provide a method for acoustically testing a work piece. It is a third objective of the present invention to provide an advantageous non-destructive testing arrangement. A fourth objective is to provide a system for acoustically testing a work piece.

An objective is solved by a method of non-destructively testing a work piece as claimed in an independent claim, a further objective is solved by a method for acoustically testing a work piece as claimed in a further independent claim. Further on an objective is solved by a non-destructive testing arrangement and an objective is solved by a system for acoustically testing a work piece. The depending claims define further developments of the invention.

The following definitions are applied for further considerations. A positioning system means an arrangement, which comprises at least one transmitter, at least one transponder and an analysing unit. In the simplest case a transponder means an indentation fixed on a particular position of a work piece.

A wind turbine blade (2) is characterised by the blade root (3), the tip (6), the leading edge (4), the trailing edge (5) and the shoulder (7). A frame of reference of a wind turbine blade (2) can be based on the span line (20) and a chord line (19) perpendicular to the span line. For illustration of the mentioned terms see FIG. 1.

The inventive method of non-destructively testing a work piece comprises the following steps. At first the work piece is placed within an active field of a positioning system. Then a frame of reference of the work piece is established based on the geometry of the work piece in the coordinates of the positioning system. The geometry of the work piece is detected by determining the position of specific transponders, which are fixed to the work piece, by the positioning system or the geometry of the work piece is detected by scanning at least parts of the contour of the work piece with a transponder of the positioning system. Now testing data is acquired for the work piece with a non-destructive testing probe, which comprises a transponder of the positioning system, while the position of the testing probe is recorded by the positioning system. The position of the testing probe is transformed into an intrinsic position defined with respect to the frame of reference of the work piece and the intrinsic position of the testing probe is assigned to the testing data recorded at the respective position.

The simultaneous recording of the non-destructive testing probe readings and the intrinsic position allows a direct coupling between the non-destructive testing probe reading and the position of the work piece irrespective of its orientation in three dimensions. The results can be stored in a database and can possibly be also presented on a screen.

Generally there is no need for the work piece to be in the same spatial orientation every time, especially for later applications. This means for instance that a work piece can be tested somewhere in the factory and can later be repaired or be tested again somewhere else, e.g. in the field. The position of a particular testing readout can be recovered independently of the actual spatial orientation of the work piece, once the frame of reference of the work piece in its actual orientation is established, since it is defined in the frame of reference of the work piece.

During the following non-destructive testing the position and assigned testing data can be stored in a database and can also be presented on a screen. The database can be created in any relevant format and can give any desirable readout, such as progressive scan, contour plots or colour-coded shading, and that can be fitted with templates, rejection criteria or alarms.

It is generally advantageous to establish the frame of reference of the work piece based on the geometry of the work piece. In the case, that a wind turbine blade is tested, for example, a meaningful frame of reference can be established by using a chord line and the span line of the blade.

For locating of the former chosen frame of reference of the work piece in its current position, the geometry of the work piece can detected by scanning at least parts of the contour of the work piece with a transponder of the positioning system, with or without the non-destructive testing probe.

One possibility is to scan the whole work piece along a typical contour. For a wind turbine blade this could be the contour from the blade root along the leading edge to the tip and back again to the root along the tailing edge. Another possibility is it to scan with the transponder only a few sufficient features or points, which allow a reproduction of the frame of reference of the work piece.

Moreover, the geometry of the work piece can also be detected by determining the position of specific transponders, which are permanently fixed to, or under the surface of, the work piece at positions which allow a reproduction of the frame of reference, by the positioning system. For a wind turbine blade this could be three permanently fixed transponders, one fixed at the blade root, a second at the tip and a third fixed at the shoulder. The locations of the transponders only need to allow for identifying the kind of blade and its orientation. Then, the frame of reference can be established based on the known orientation and the known identity of the blade.

Moreover, a wind turbine rotor comprising a hub and at least three rotor blades, which are fixed to the hub, can be tested. In this case at least three transponders, each located in the region of a tip of a rotor blade, can be used to establish the frame of reference.

The three transponders, which are used to establish the frame of reference, can be designed to be transmitters and the transponder which is assigned to the testing probe can be designed to be a base station which emits electromagnetic waves in the directions of the transmitters and the electromagnetic waves are reflected by the transmitters in the direction of the base station.

Alternatively, the transponder which is assigned to the testing probe may be designed to be a transmitter and the transponders which are used to establish the frame of reference may be designed to be base stations which emit electromagnetic waves in the direction of the transmitter and the electromagnetic waves are reflected by the transmitter in the direction of the base stations.

Advantageously, an ultrasonic testing probe is used. The ultrasonic testing probe may be designed as an ultrasonic sensor wheel with a tread penetrable for ultrasonic waves. The ultrasonic pulses can be emitted through the tread into the work piece and the reflected fraction is received.

Moreover, an additional transponder located at the hub can be used in establishing the frame of reference.

Generally, the testing data recorded at the respective position may be compared with reference testing data. The testing data recorded at the respective position can be compared with reference testing data, for instance testing data recorded before mounting the wind turbine rotor on a wind turbine. A difference in the material properties before and after mounting the rotor can be determined by comparing the recorded testing data with the reference testing data.

The non-destructive testing probe comprising the transponder can further comprise the analysing unit and/or a display, which shows the coordinates of the position and/or the non-destructive testing probe readout during the testing process. Moreover, the analysis of position and/or testing data can be done with a PC. The testing can be done manually or with a tool, e.g. a robot or a small vehicle for positions possibly difficult to reach otherwise.

Of course, the non-destructive testing and simultaneously position recording can also be done before establishing the frame of reference of the work piece in the coordinates of the positioning system.

When the testing is done it is possible to make any desired plot, e.g. contour plots of non-destructive testing reading versus position, sections in any direction, and so on. If necessary, one can go back and redo anything that was not properly tested or one can test a particular feature again. Upon completion of the testing a record with the position data and the corresponding non-destructive testing readout data can be generated automatically.

The inventive method can be repeated elsewhere, including in the field, e.g. on a wind turbine blade mounted on a wind turbine. In such case the transmitters of the positioning system may be placed on the ground in suitable locations giving a good three-dimensional fix on any location of the blade surface, e.g. when the blade is pointing vertically downwards. The actual testing can than be done by a person rappelling down the blade, thereby eliminating any need for expensive cranes or even blade demounting. The scanning can also be done by a crane, of course.

The inventive method for acoustically testing a work piece comprises the following steps. Ultrasonic pulses are emitted into the work piece by use of an ultrasonic testing probe which comprises at least one transponder for ultrasonic waves with at least one ultrasonic converter and which is moved along a surface of a work piece. Fractions of the ultrasonic pulses which are reflected by the work piece are received and converted into measurement signals $M_i$ corresponding to the reflected fractions. The material properties of the work piece are then determined by means of the measurement signals $M_i$. The position $\vec{r}_i$ of the ultrasonic testing probe is determined in a frame of reference in which the work piece is statically placed by means of a positioning system. The positioning system comprises at least four transponders for electromagnetic radiation. At least three of the four transponders have a constant distance to each other and establish the frame of reference. The ultrasonic testing probe is equipped with at least one of the transponders. The position $\vec{r}_i$ of the ultrasonic testing probe is determined by measuring the propagation delay of electromagnetic waves which are emitted and received by the transponders between the at least three transponders which establish the frame of reference and the at least one transponder which is assigned to the ultrasonic testing probe. The determined measurement signals $M_i$ are assigned to the determined positions $\vec{r}_i$ by means of a cartography unit and the assigned signals $M_i(\vec{r}_i)$ are saved on a medium assigned to the cartography unit.

The transponders which establish the frame of reference may be designed to be transmitters and the transponder which is assigned to the ultrasonic testing probe may be designed to be a base station which emits electromagnetic waves in the directions of the transmitters. Then the electromagnetic waves are reflected by the transmitters in the direction of the base station.

Alternatively, the transponder which is assigned to the ultrasonic testing probe can be designed to be a transmitter and the transponders which establish the frame of reference can be designed to be base stations which emit electromagnetic waves in the direction of the transmitter. Then the electromagnetic waves are reflected by the transmitter in the direction of the base stations.

Preferably the ultrasonic testing probe is designed to be an ultrasonic sensor wheel with a tread and the ultrasonic pulses are emitted through the tread into the work piece and the reflected fractions are received again.

For example, the material properties of a wind turbine rotor blade as work piece can be determined. In this case each transponder of the transponders which establish the frame of reference may be mounted in the region of a tip of a rotor blade which is fixed to a hub of a wind turbine which comprises at least three rotor blades.

Advantageously, an additional transponder is provided for use in establishing the frame of reference. The additional transponder may preferably be mounted at the hub.

The signals $M_i(\vec{r}_i)$ which are determined at the wind turbine (150) can be compared with reference signals $M_{ref,i}(\vec{r}_i)$ which were determined before mounting the rotor blade on the wind turbine. Then, difference in the material properties before and after mounting the rotor blade can be determined.

The inventive non-destructive testing arrangement comprises a non-destructive testing probe equipped with a transponder for a positioning system. It further comprises a positioning system with at least one transponder or transmitter, which emits directional radiation the direction of which can be controlled, or it further comprises a positioning system with at least two transponders or transmitters, which emit non-directional radiation.

Advantageously, the positioning system can comprise 3 or more transmitters. A PC can be used as an analysing unit for the positioning system and/or the non-destructive testing probe. Alternatively, the non-destructive testing arrangement can make use of a publicly available positioning system, like e.g. GPS.

Generally, the positioning system can be a GPS (Global Positioning System), a differential GPS, an ultrasonic positioning system, a laser positioning system, a radar positioning system, etc. Further, a wireless display can be attached to the positioning system transponder.

Additionally, the inventive non-destructive testing arrangement can comprise a database for storing the position and the assigned testing data in a format that gives progressive scan, contour plots or colour-coded shading, and that can be fitted with templates, rejection criteria or alarms.

The non-destructive testing probe can for example be an ultrasonic probe, an x-ray probe, a nuclear magnetic resonance probe, a heat flow direction probe, etc.

If the non-destructive testing probe is an ultrasonic testing probe, then the ultrasonic testing probe can comprise at least a transponder for ultrasonic waves and an analysing unit. The transponder for ultrasonic waves comprises at least one ultrasonic converter. The transponder is moveable along a surface of a work piece. Ultrasonic pulses are emittable into the work piece by means of the transponder. A fraction of the ultrasonic pulses which is reflected by the work piece is receivable and convertable to an electrical measurement signal $M_i$. The ultrasonic testing probe further comprises an analysing unit for determining the material properties of the work piece by means of the measurement signals $M_i$.

Preferably the positioning system may comprise at least four transponders for electromagnetic radiation and an analysing unit for determining the position $\vec{r}_i$ of the ultrasonic testing probe. At least three of the transponders may have a constant distance to each other and may establish a frame of reference in which a work piece is statically placed. The ultrasonic testing probe can be equipped with at least one transponder. The analysing unit can be used for determining the position $\vec{r}_i$ of the ultrasonic testing probe in the frame of reference by means of a measurement of the propagation delay of electromagnetic waves which are emitted and received by the transponders between the at least three transponders which establish the frame of reference and the at least one transponder which is assigned to the ultrasonic testing probe.

The positioning system may further comprise a cartography unit for assigning a determined measurement signal $M_i$ to a determined position $\vec{r}_i$ and for saving the assigned signal $M_i(\vec{r}_i)$ on a medium assigned to the cartography unit.

The transponders which establish the frame of reference can be transmitters and the transponder which is assigned to the testing probe can be a base station for emitting electromagnetic waves in the directions of the transmitters. Then the transmitters can reflect the electromagnetic waves in the direction of the base station.

Alternatively, the transponder which is assigned to the testing probe can be a transmitter and the transponders which establish the frame of reference can be base stations for emitting electromagnetic waves in the direction of the transmitter. The transmitter can reflect the electromagnetic waves in the direction of the base stations.

The ultrasonic testing probe can be designed as an ultrasonic sensor wheel with a tread penetrable for ultrasonic waves. The ultrasonic pulses can be emittable through the tread into a work piece and the reflected fraction can be receivable.

The work piece may, for example, be a wind turbine rotor blade. In this case each transponder of the transponders which establish a frame of reference may be located in the region of a tip of a rotor blade which is fixed to a hub of a wind turbine. The wind turbine may comprise at least three rotor blades. The hub can comprise an additional transponder which can be used in establishing the frame of reference.

The advantages of the inventive method of non-destructively testing a work piece and the inventive non-destructive testing arrangement are the following. The described method and the described arrangement allow a precise correlation between non-destructive testing readout and probe position in the reference frame of the work piece, especially for the testing of large structures. Moreover, the structure can be tested in every position, as long as this position can be reached with the non-destructive testing probe. This eliminates any need for expensive cranes or even demounting of the structure.

Further, for later purposes, especially for the repair, the location of a particular non-destructive testing readout is easy to recover once the frame of reference is established for the actual orientation. The recovering can also be done using the inventive method or the inventive non-destructive testing arrangement. For the purpose of the recovering of particular positions it is of course possible to use only the described positioning system without the non-destructive testing probe.

The inventive system for acoustically testing a work piece comprises at least an ultrasonic testing probe, a positioning system and a cartography unit. The ultrasonic testing probe comprises at least a transponder for ultrasonic waves and an analysing unit. The transponder for ultrasonic waves comprises at least one ultrasonic converter. It is moveable along a surface of a work piece. Ultrasonic pulses are emittable into the work piece by means of the transponder for ultrasonic waves. Fractions of the ultrasonic pulses which are reflected by the work piece are receivable and convertable to an electrical measurement signal $M_i$. The analysing unit is used for determining the material properties of the work piece by means of the measurement signals $M_i$.

The positioning system comprises at least four transponders for electromagnetic radiation and an analysing unit for determining the position $\vec{r}_i$ of the ultrasonic testing probe. At least three transponders of the four transponders have a constant distance to each other and establish a frame of reference in which the work piece is statically placed. The ultrasonic testing probe is equipped with at least one transponder. The analysing unit is used for determining the position $\vec{r}_i$ of the ultrasonic testing probe in the frame of reference by means of a measurement of the propagation delay of electromagnetic waves which are emitted and received by the transponders between the at least three transponders which establish the frame of reference and the at least one transponder which is assigned to the ultrasonic testing probe.

The cartography unit is used for assigning the determined measurement signals $M_i$ to the determined position $\vec{r}_i$ and for saving the assigned signals $M_i(\vec{r}_i)$ on a medium assigned to the cartography unit.

The transponders which establish the frame of reference can be transmitters and the transponder which is assigned to the ultrasonic testing probe can be a base station. The base station may be designed for emitting electromagnetic waves in the directions of the transmitters and the transmitters may be designed for reflecting the electromagnetic waves in the direction of the base station.

Alternatively, the transponder which is assigned to the ultrasonic testing probe can be a transmitter and the transponders which establish the frame of reference can be base stations. The base stations may be designed for emitting electromagnetic waves in the direction of the transmitter and the transmitter can be designed for reflecting the electromagnetic waves in the direction of the base stations.

Preferably, the ultrasonic testing probe may be designed as an ultrasonic sensor wheel with a tread penetrable for ultrasonic waves. Ultrasonic pulses can be emitted through the tread into the work piece and the reflected fraction can be received.

The work piece may, for example, be a wind turbine rotor blade. In this case each of the transponders which establish the frame of reference can be located in the region of a tip of a rotor blade which is fixed to a hub of a wind turbine which may comprise at least three rotor blades. The hub may comprise an additional transponder which is used in establishing the frame of reference.

The combination of an ultrasonic testing probe with a positioning system allows for assigning the measurement signals $M_i$ to a position $\vec{r}_i$ at the work piece by means of the cartography unit. Thus, a map about the material properties of the work piece can be obtained. This map can be used as a basis for quality control of the work piece, because measurement data recorded at different times can be compared with each other.

BRIEF DESCRIPTION OF THE DRAWINGS

Further features, properties and advantages of the present invention will become clear from the following description of embodiments in conjunction with the accompanying drawings.

FIG. 3 schematically shows a wind turbine blade and two transmitters in a frontal view.

FIG. 4 schematically shows a wind turbine blade equipped with permanent transponders and a local positioning system in a perspective view.

FIG. 6 schematically shows an ultrasonic sensor wheel located at the rotor blade in a sectional view perpendicular to the rotation axis of the ultrasonic sensor wheel.

FIG. 7 schematically shows the ultrasonic sensor wheel on the rotor blade in a sectional view, connected to a control unit, an analysis unit, and a cartography unit.

FIG. 8 schematically shows the inventive system for acoustically testing a rotor blade located on a wind turbine.

DETAILED DESCRIPTION OF INVENTION

Figure 1:
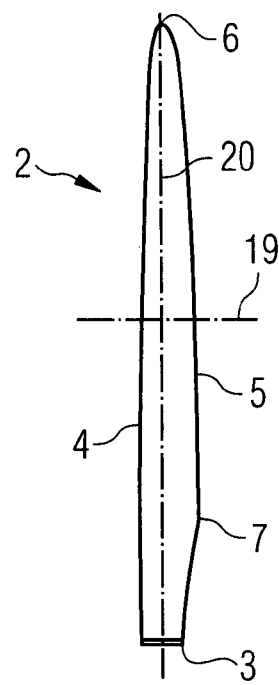
FIG. 1 shows a wind turbine blade in a plan view onto the plane defined by the blade's span and the blade's chord.

FIG. 1 shows a wind turbine blade (2) in a plan view onto the plane defined by the blade's span and the blade's chord. One can see the blade root (3), the tip (6), the leading edge (4), the trailing edge (5) and the shoulder (7). A frame of reference of a wind turbine blade (2) can, e.g., be based on the span line (20) and a chord line (19) perpendicular to the span line.

Figure 2:
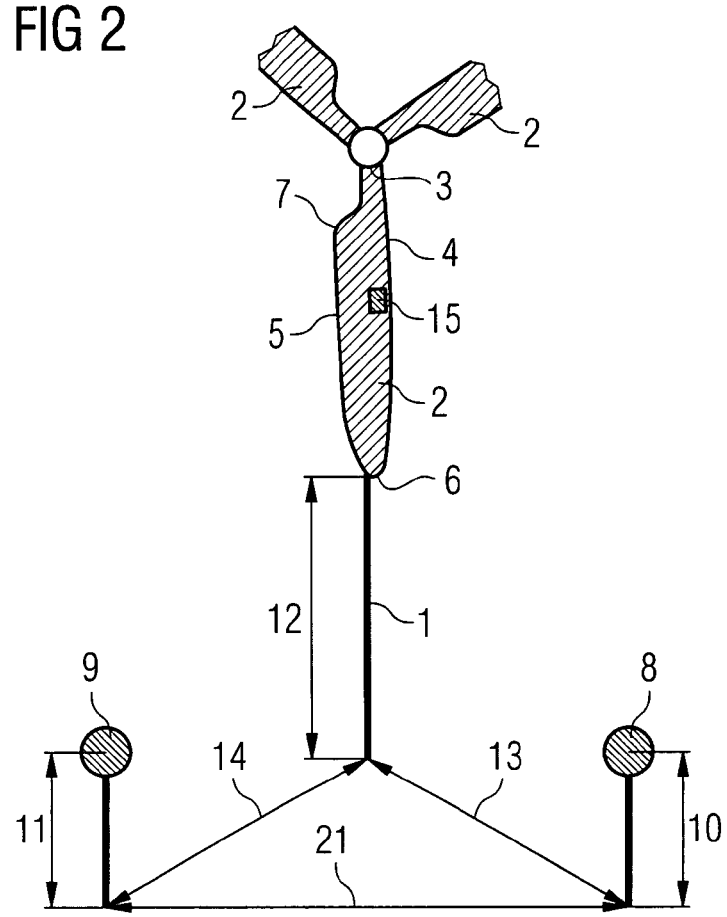
FIG. 2 schematically shows a wind turbine blade with a local positioning system in a perspective view.

A first embodiment of the inventive method will now be described in more detail with respect to FIGS. 2 and 3. FIG. 2 schematically shows a wind turbine (1) equipped with three wind turbine blades (2) in the field in a perspective view. Characteristic geometrical features of a wind turbine blade are the root (3), the leading edge (4), the trailing edge (5), the tip (6) and the shoulder (7).

The exact size and shape of the wind turbine blade is either known from the manufacturer or the characteristic features of the blade were measured or scanned by a local positioning system before mounting the blade on the wind turbine. As a frame of reference for all subsequent measurements the location of the span line in the blade root is used as origin and the plane containing the span line (20) and the chord line (19) in the root are used in the present embodiment. However, other origins than the root can be used as well.

Now one side of the blade is to be two-dimensionally scanned by a non-destructive testing probe. Non-destructive testing probe readout as well as the corresponding two-dimensional probe position shall be recorded. The non-destructive testing probe can be an ultrasonic probe, an x-ray probe, a nuclear magnetic resonance probe or a heat flow direction probe, respectively. In the present embodiment an ultrasonic probe is used. First a transponder of a positioning system, for instance a radar system comprising two transmitters which emit non-directed radiation, is installed and calibrated. Further an analysing unit, here for example a PC, is installed, initialized and wirelessly connected with the non-destructive testing probe (15) comprising the transponder. For achieving well-defined results regarding the probe position, the two transmitters (8) and (9) should be placed in a height (10), (11) which is smaller than the minimal height (12) of the tip (6).

The reason for this is illustrated in FIG. 3. A transmitter emitting non-directed radiation is only able to measure the distance to the detected probe (15) comprising the transponder. This means, that the detected probe (15) can generally be located only on the surface of a sphere. The use of a second transmitter reduces the possible location of the probe (15), which is detected by both transmitters. The probe (15) can be located only at positions where the spheres of the two transmitters regarding the measured distance intersect. However, if the transmitters are placed in particular distances (13), (14) to the wind turbine and have a known distance (21) to each other, then this information allows it to reduce the possible probe locations to two points, where the two spheres can intersect.

In FIG. 3 the two transmitters (8) (9) and the blade (2) of FIG. 2 are schematically shown in a front view. The left circle (22) indicates the possible locations of the probe as detected by the left transmitter (9). The right circle (23) indicates the possible locations of the probe as detected by the right transmitter (8). The intersection point (24) is detected by both transmitters and corresponds to the actual position of the probe (15) on the blade (2). But there is a second intersection point (25) in the plane of the blade, which is also detected by both transmitters and therefore could also be the actual position of the probe (15). If the tip (6) of the blade is placed in a height (12), which is at least the height (10) (11) of each transmitter (8) (9), then the point (25) can be excluded as possible position of the probe.

The blade which is to be scanned should preferably hang vertically downwards. Then the non-destructive testing probe (15) comprising the transponder of the local positioning system, is moved around characteristic geometrical features of the blade. This can be done with a tool or manually by a person rappelling down the blade by moving the probe (15) from the blade root (6) along the leading edge (4) to the tip (6), and back again to the root along the trailing edge (5). With these data the actual position of the frame of reference of the turbine blade in the field is fixed and each position of the testing probe can be transformed into an intrinsic position defined with respect to this frame of reference.

Next, the blade is tested with the non-destructive testing probe (15) comprising the transponder. The intrinsic position of the testing probe is assigned to the testing data recorded at the respective position, for example by use of the PC. Again, the testing can be done manually by a person rappelling down the blade or with a tool. The testing probe can further have a display which shows the coordinates of the actual probe position and possibly also the probe readout. While the blade is tested, all data concerning probe position and non-destructive testing probe readout are recorded simultaneously and are stored on the PC.

When the testing is done it is possible to make any desired plot, e.g. contour plots of non-destructive testing reading versus position, sections in any direction, and so on. Anything that was not properly tested can now immediately be tested again. The general result of the testing is a coupling between non-destructive testing probe readout and the two-dimensional position on the blade.

Alternatively, for getting a three-dimensional coupling between non-destructive testing probe readout and intrinsic position on the blade, three of the former described transmitters can be used. In this case all three transmitters can be installed in an arbitrary height, as long as the blade is placed in the active field of the transmitters.

A second embodiment of the inventive method will be described with reference to FIG. 4. Elements corresponding to elements of the first embodiment will be designated with the same reference numeral and will not be described again.

Now a three-dimensional coupling between non-destructive testing probe readout and intrinsic position on a wind turbine blade is described. Before mounting the turbine blade a set of permanent transponders (16), e.g. radar transponders in the present embodiment, were fixed on the blade at positions which allow an identification of the frame of reference. For example, one permanent transponder was fixed at the blade root (3) on the side towards the leading edge (4), a second transponder was fixed at the tip (6) and a third on the shoulder (7). This is shown in FIG. 4. One can see in FIG. 3 the wind turbine (1) of FIG. 2 with turbine blades (2) which are equipped with three permanent transponders (16) and surrounded by three transmitters (17). Additionally, a crane (18) is shown which moves the non-destructive testing probe with transponder (15) for the testing.

For the further measurement three radar transmitters (17) will be placed in the field around the wind turbine. Before testing, the position of the permanent transponders is recorded. Then the blade is tested with the non-destructive testing probe comprising a radar transponder (15) using a crane (18) or a robot to reach the mounted turbine blade. This is also shown in FIG. 4. As described in the first embodiment, all data concerning probe position and non-destructive testing probe readout are recorded simultaneously. The obtained result is a coupling between non-destructive testing probe readout and the three-dimensional position on the blade. Of course, instead of using a crane, a technician could rappel from the hub of the rotor.

Although non-directed transmitters were used in the embodiment it is also possible to use transmitters which send out directed radiation, e.g. a laser beam, and in which the direction into which the radiation is sent out can be varied and measured. Then, only one transmitter would be enough since the angle at which the radiation is sent out can be detected directly from the transmitter and the distance of the transponder, e.g. a simple reflector, can be established based on, e.g. interferometric measurements or time delay of returning laser pulses. With knowing the angle and the distance, the three-dimensional position of the reflector at the probe (or a reflector permanently fixed to the blade) can be established with respect to the transmitter. After scanning, e.g. the contour of the blade for establishing its frame of reference, the intrinsic position of the testing probe in the blade's frame of reference can be assigned to the testing date of the testing probe.

Now a third embodiment of the present invention will be described with reference to FIGS. 5 to 8. In the FIGS. 5 to 8 corresponding elements are designated with the same reference numerals.

Figure 5:
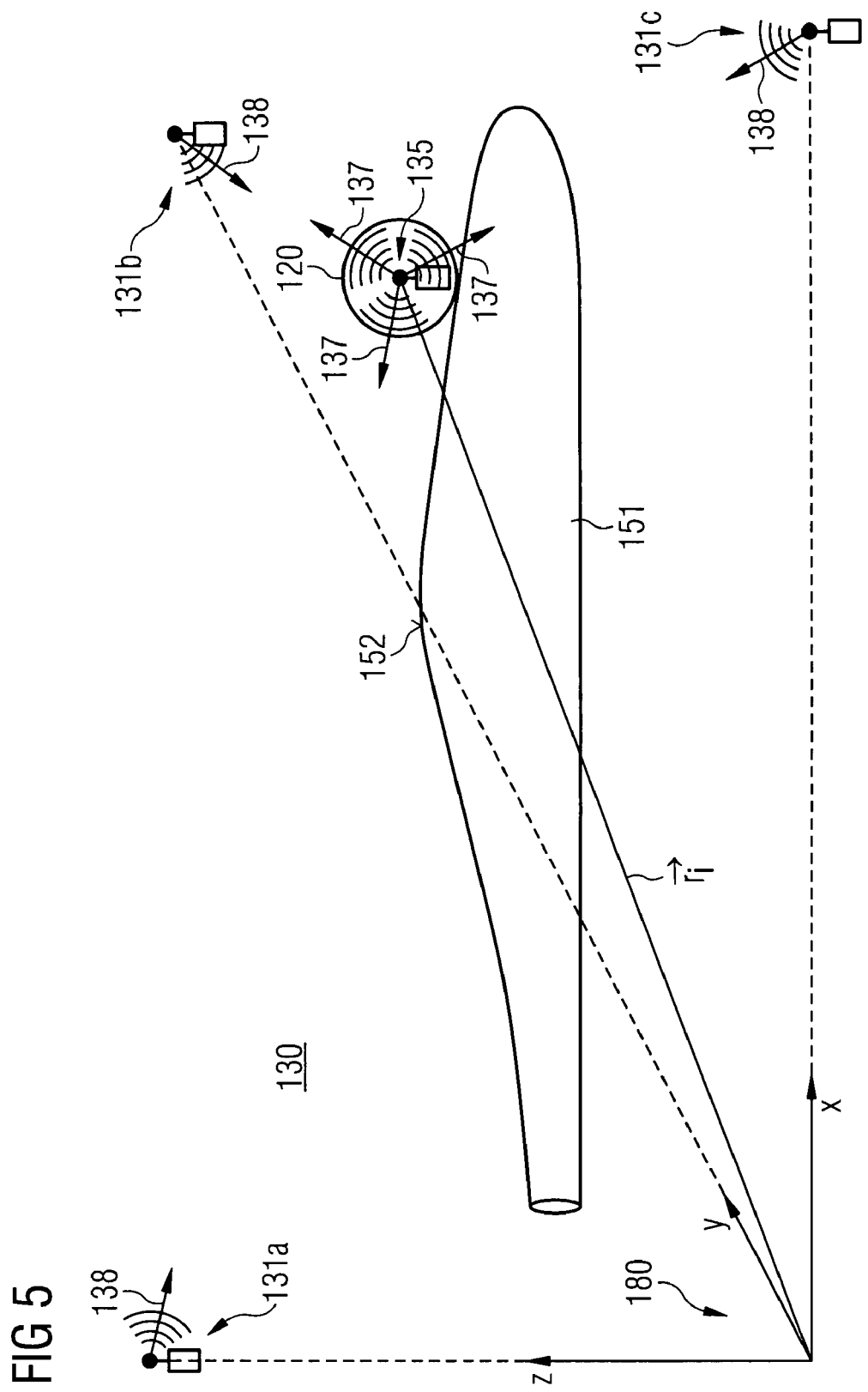
FIG. 5 schematically shows a system for acoustically testing a rotor blade.

FIG. 5 schematically shows a system for acoustically testing a rotor blade 151. The inventive system comprises an ultrasonic testing probe 120 which is designed as an ultrasonic sensor wheel, a positioning system 130 and a cartography unit 140. In the present embodiment the positioning system 130 comprises four transponders 131a, 131b, 131c, 135. Three transponders 131a, 131b, 131c of the four transponders 131a, 131b, 131c, 135 have a constant distance to each other and establish a frame of reference which is illustrated in FIG. 1 as a coordinate system 180 with axes x, y, and z. The axes x, y, and z are perpendicular to each other.

The rotor blade 151 is stationary placed in the coordinate system 180. The ultrasonic sensor wheel 120 can be rolled along the surface 152 of the rotor blade 151 to investigate the material properties of a rotor blade. The ultrasonic sensor wheel 120 comprises the fourth transponder 135. This transponder 135 is moved relatively to the three transponders 131a, 131b, 131c which establish the frame of reference 180. The transponder 135 which is assigned to the ultrasonic sensor wheel 120 is moved such that the relative distance between the transponder 135 and at least one of the three transponders 131a, 131b, 131c which establish the frame of reference 180 changes.

The position $\vec{r}_i$ of the transponder 135 which is assigned to the ultrasonic sensor wheel 120 is determined in the frame of reference 180, when the three distances between the transponder 135 and the transponders 131a, 131b, 131c are known. The position of the ultrasonic sensor wheel 120 in the frame of reference 180 is then also determined. The distance between the transponder 135 and one of the transponders 131a, 131b, 131c is determined by measuring the time in which an electromagnetic wave 137, 138 covers twice the distance between the transponder 135 and one of the transponders 131a, 131b, 131c.

The transponder 135 which is assigned to the ultrasonic sensor wheel 120 can, for example, be a base station, as it is shown in FIG. 1. In this case the base station emits electromagnetic waves 137 in the direction of the transponders 131a, 131b, 131c which establish the frame of reference 180. In the present example the transponders 131a, 131b, 131c are transmitters. The electromagnetic waves 137, 138 are reflected by the transmitters 131a, 131b, 131c after covering the distance between the base unit 135 and the transmitters 131a, 131b, 131c. Then the electromagnetic waves 137, 138 again cover the distances between the base unit 135 and the transmitters 131a, 131b, 131c and are received by the base unit 135.

To distinguish between the electromagnetic waves 138 which are reflected by different transmitters 131a, 131b, 131c and are received from different directions, the electromagnetic waves 138 are charged with an identification signal by the particular transmitter 131a, 131b, 131c when the electromagnetic waves 138 are reflected. The electromagnetic waves 138 can, for instance, be modulated or superposed to achieve an identification. The corresponding three propagation times are determined by means of an analysing unit 136 which is assigned to a positioning system 130. The position $\vec{r}_i$ of the base station 135 and of the ultrasonic sensor wheel 120 is determined by means of the detected propagation times.

Alternatively, the transponders 131a, 131b, 131c which establish the frame of reference 180 may be base stations, while the transponder 135 which is assigned to the ultrasonic sensor wheel 120 is a transmitter.

FIG. 6 schematically shows the ultrasonic sensor wheel 120 in a sectional view perpendicular to the axis 203 of the wheel. The ultrasonic sensor wheel 120 comprises a sufficient massive hollow cylinder 205 which is penetrable for ultrasound. The hollow cylinder 205 comprises a tread 122 which is put on the surface 152 of the rotor blade for performing the measurement.

The material of the hollow cylinder 205 should have good ultrasound properties to provide a good sound coupling. Moreover, the material should be able to hold out against high mechanical and thermal loads. For this purpose an elastic material should preferably be used, for example EPDM (ethylene-propylene-Dien-monomer), a polymer of ethylene, propylene, and a smaller fraction of Dien.

Inside the ultrasonic sensor wheel 120 a cavity 204 is formed, which is filled with a medium which is penetrable for ultrasonic. The axis 203 of the wheel comprises a cylindrical box 201 which extends radially outwards and which is located inside the ultrasonic sensor wheel 120. The box 201 is filled with air, for example, and is sealed against the cavity 204 which is filled with the coupling medium. A transponder for ultrasound 121 which is assigned to an ultrasonic converter 123 is placed in the box 201. The box 201 may also comprise more than one transponder 121 for ultrasound. The box 201 additionally comprises the transponder 135 which is a base station of the positioning unit 130. The axis 203 of the wheel comprises a bore 202 through which a lead 206 is led outwards. The lead 206 may be, for example, a control lead or a signal lead of the transponder 121 and base station 135 inside the ultrasonic sensor wheel 120.

FIG. 6 schematically shows the "pulse-echo"-method as an example for a measuring method. In this case the used ultrasonic converter 123 must be able to emit and to receive ultrasound. An ultrasound pulse 124 is emitted from the converter 123 in direction of the rotor blade 151, for example perpendicular to the surface 152 of the rotor blade 151, and is reflected at the rotor blade 151. A fraction of the reflected ultrasound pulses 125 is then received by the converter 123. In the converter 123 the received ultrasound pulse 125 is converted into an electrical signal and is transferred through the lead 206 to a signal processing unit 127. If the whole rotor blade 151 shall be tested, then the ultrasonic sensor wheel 120 is moved along the surface 152 of the rotor blade 151 with its tread 122, while the converter 123 does not change its orientation relative to the rotor blade 151.

The "pitch-catch"-method is another measuring method, which is not shown in the figures. In the "pitch-catch"-method at least two ultrasonic converters 123 are used which are located in the box 201. One of the converters emits an ultrasound pulse 124 in the direction of the rotor blade 151 which is reflected at the rotor blade 151. A fraction of the reflected ultrasound pulse 125 is then received by the second converter 123 which is used as a receiver. The received ultrasound pulse 125 is then converted into an electrical signal and is transferred to the signal processing unit 127 by means of the lead 206.

To detect horizontal defects, as for example inclusions or delaminations, the ultrasound pulses 124 should advantageously be perpendicularly radiated onto the surface 152. Defect structures which are vertically orientated relative to the surface 152 of the rotor blade can preferably be detected by means of an inclined radiation of the ultrasound pulses 124.

FIG. 7 schematically shows an example for the inventive system for acoustically testing a rotor blade. The ultrasonic sensor wheel 120 is shown in a sectional view along the axis 203. The ultrasonic sensor wheel 120 is placed on the surface of the rotor blade 151. A control unit 128, an analysing unit 126 and a cartography unit 140 are connected to the ultrasonic sensor wheel 120. The box 201 comprises a transponder 121 which is provided with an ultrasonic converter 123.

The converter 123 is connected to a switching element 129 by means of a lead 206. The switching element 129 switches the converter 123 in an emission mode or a receive mode. The switching element 129 is controlled by means of the control unit 128. A send-receive switch can be used instead of the switching element 129. The control unit 128 comprises a send pulser and a send amplifier. In FIG. 3 the emission mode is switched on. In this case the converter 123 is provided with amplified send pulses by means of the send pulser which is connected with the send amplifier. If the receive mode is switched on, then the electrical signals which were converted in the converter 123 are transferred to the signal processing unit 127.

The signal processing unit 127 comprises, for instance, a receive amplifier with time-gain correction and an analogue filter. The receive amplifier amplifies, normalises, and filters the signals from the converter 123. An interference limiting is achieved by means of the filter. The signal is then transferred for digitisation to an analogue/digital converter, which may be located in a signal processing means. The digital signals are further analysed by means of an analysing means 126 with a digital signal processor by further reducing the digitised data by means of digital filters. A software which is assigned to the digital signal processor analyses the signals, especially with the aim of determining and recording surface defects at the rotor blade 151 and displaying corresponding measurement signals $M_i$. The material properties of the rotor blade 151 at the position $\vec{r}_i$ can be determined by means of the measurement signals $M_i$. The obtained measurement signals $M_i$ can be reduced by means of digital compression to reduce the data rate.

The position of the ultrasonic sensor wheel 120 in the frame of reference 180 and also the position $\vec{r}_i$ of the measurement at the rotor blade 151 are determined by means of the base station 135 which is attached to the ultrasonic sensor wheel 120 and by means of the analysing unit 136 which is connected to the base station 135. The results $M_i$ and $\vec{r}_i$ are transferred to the cartography unit 140, for example by means of an electric connexion or wirelessly by means of infrared or radio. The combination of the measurement signals $M_i$ with the position $\vec{r}_i$ is performed in an allocation unit 141. The measurement signals $M_i(\vec{r}_i)$ which are assigned to particular positions $\vec{r}_i$ of the measurement are transferred to a medium 142, for instance a memory card or a hard disc, and are saved there. After completely testing the rotor blade 151a complete map of the material properties of the rotor blade 151 is stored on the medium 142.

Additionally, reference signals $M_{ref,i}(\vec{r}_i)$ are saved on the medium 142. The reference signals $M_{ref,i}(\vec{r}_i)$ were recorded after manufacturing the rotor blade 151. The reference signals $M_{ref,i}(\vec{r}_i)$ are compared with later recorded measurement signals $M_i(\vec{r}_i)$, for example by calculating the difference, by means of a signal processor unit 143 which is connected with the medium 142. This is, for example, done to distinguish between new defects of the material and defects that were already present shortly after manufacturing. The allocation unit 141, the medium 142, and the signal processing unit 143 are parts of the cartography unit 140.

FIG. 8 schematically shows the inventive system for acoustically testing a rotor blade 151 at a wind turbine 150. The wind turbine 150 comprises a tower 155 and a nacelle which is rotatably mounted onto the tower 155. The nacelle comprises a rotor with a substantially horizontal rotor shaft which is connected to the nacelle. The rotor comprises a hub 154 and three rotor blades 132 which are fixed to the hub 154. Each of the rotor blades 132 comprises a transmitter 131a, 131b, 131c, which can also be a transponder. The transmitters 131a, 131b, 131c are mounted on the rotor blade 132 in the area where the tips 153 of the rotor blades 132 are located. The transmitters 131a, 131b, 131c establish the frame of reference 180. One of the rotor blades 151 is orientated parallel to the tower 155 and is tested by means of the ultrasonic sensor wheel 120 which is equipped with the base station 135. A map about the material properties of the whole rotor blade 151 is then determined by means of the inventive system. The hub 154 comprises an additional transmitter 131d, which can also be a transponder. This is advantageous because near the tip 153 of a rotor blade the distance between the ultrasonic sensor wheel 120 and the transmitter 131c which is placed at the particular tip 153 can either not precisely be measured or can not be measured at all. The additional transmitter 131d allows for a precise determination of the position $\vec{r}_i$ of the ultrasonic sensor wheel 120.

The invention claimed is:

1. A method of non-destructively testing a work piece, comprising:
   placing the work piece within an active field of a positioning system;
   detecting a geometry of the work piece by a step selected from the group consisting of:

determining a position of specific transponders fixed to the work piece, by the positioning system, and scanning at least parts of the contour of the work piece with a transponder of the positioning system;

establishing a frame of reference of the work piece based on the geometry of the work piece in coordinates of the positioning system;

acquiring testing data for the work piece with a non-destructive testing probe, wherein the probe has a transponder of the positioning system, while the position of the testing probe is recorded by the positioning system;

transforming the position of the testing probe into an intrinsic position defined with respect to the frame of reference of the work piece; and assigning the intrinsic position of the testing probe to the testing data recorded at the respective position, wherein an ultrasonic testing probe is used, wherein the ultrasonic testing probe has an ultrasonic sensor wheel with a tread penetrable for ultrasonic waves, and wherein ultrasonic pulses are emitted through the tread into the work piece, wherein a reflected fraction is received.

2. The method as claimed in claim 1, wherein the position and assigned testing data are stored in a format that gives progressive scan, contour plots or color-coded shading, and that can be fitted with templates, rejection criteria or alarms.

3. The method as claimed in claim 1, wherein a wind turbine blade is tested.

4. The method as claimed in claim 3, wherein a chord line and a span line of the blade are used as frame of reference of the blade.

5. The method as claimed in claim 1, wherein a wind turbine rotor comprising a hub and at least three rotor blades, which are fixed to the hub, is tested.

6. The method as claimed in claim 5, wherein at least three transponders, each located in the region of a tip of each one of said at least three rotor blades, are used to establish the frame of reference.

7. A method of non-destructively testing a work piece, comprising:

placing the work piece within an active field of a positioning system;

detecting a geometry of the work piece by a step selected from the group consisting of:

determining the position of specific transponders fixed to the work piece, by the positioning system, and scanning at least parts of the contour of the work piece with a transponder of the positioning system;

establishing a frame of reference of the work piece based on the geometry of the work piece in coordinates of the positioning system;

acquiring testing data for the work piece with a non-destructive testing probe, wherein the probe has a transponder of the positioning system, while the position of the testing probe is recorded by the positioning system;

transforming the position of the testing probe into an intrinsic position defined with respect to the frame of reference of the work piece; and assigning the intrinsic position of the testing probe to the testing data recorded at the respective position, wherein the testing data recorded at the respective position are compared with reference testing data, wherein a wind turbine rotor comprising a hub and at least three rotor blades, which are fixed to the hub, is tested, wherein the testing data recorded at the respective position are compared with reference testing data which were recorded before mounting the wind turbine rotor on a wind turbine, and wherein a difference in the material properties before and after mounting the rotor is determined by comparing the recorded testing data with the reference testing data.

8. The method as claimed in claim 7, wherein the position and assigned testing data are stored in a format that gives progressive scan, contour plots or color-coded shading, and that can be fitted with templates, rejection criteria or alarms.

9. The method as claimed in claim 7, wherein at least three transponders, each located in the region of a tip of each one of said at least three rotor blades, are used to establish the frame of reference.

* * * * *